US010792155B2

(12) United States Patent
Perez et al.

(10) Patent No.: US 10,792,155 B2
(45) Date of Patent: Oct. 6, 2020

(54) THREADED INSERT FOR IMPLANT

(71) Applicant: Howmedica Osteonics Corp., Mahwah, NJ (US)

(72) Inventors: Alvin Perez, Ringwood, NJ (US); Philip Harris Frank, Maplewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 51 days.

(21) Appl. No.: 16/162,871

(22) Filed: Oct. 17, 2018

(65) Prior Publication Data

US 2019/0117405 A1  Apr. 25, 2019

Related U.S. Application Data

(60) Provisional application No. 62/574,407, filed on Oct. 19, 2017.

(51) Int. Cl.
*A61F 2/34* (2006.01)
*A61F 2/30* (2006.01)
*A61F 2/46* (2006.01)

(52) U.S. Cl.
CPC ............ *A61F 2/34* (2013.01); *A61F 2/30749* (2013.01); *A61F 2/4609* (2013.01); *A61F 2/4637* (2013.01); *A61F 2002/3079* (2013.01); *A61F 2002/30224* (2013.01); *A61F 2002/30332* (2013.01); *A61F 2002/30774* (2013.01); *A61F 2002/30797* (2013.01); *A61F 2002/30886* (2013.01); *A61F 2002/3401* (2013.01); *A61F 2002/3469* (2013.01); *A61F 2230/0069* (2013.01); *A61F 2250/0026* (2013.01)

(58) Field of Classification Search
CPC ...... A61F 2/28; A61F 2/30; A61F 2/34; A61F 2/4609; A61F 2/4637; A61F 2/30749
See application file for complete search history.

(56) References Cited

U.S. PATENT DOCUMENTS

| 1,182,826 A | 5/1916 | Wilbanks |
| 1,197,929 A | 9/1916 | Gordon |
| 1,231,140 A | 6/1917 | Dixon |
| 1,286,403 A | 12/1918 | Piggins |
| 1,352,567 A | 9/1920 | Wettervik |
| 1,472,020 A | 10/1923 | Holmes |
| 1,520,904 A | 12/1924 | Keim |
| 1,559,955 A | 11/1925 | Glover et al. |
| 1,627,172 A | 5/1927 | Gouirand et al. |
| 1,876,836 A | 9/1932 | Berge |
| 1,933,251 A | 10/1933 | Gauthier |

(Continued)

*Primary Examiner* — Jason-Dennis N Stewart
(74) *Attorney, Agent, or Firm* — Lerner, David, Littenberg, Krumholz & Mentlik, LLP

(57) ABSTRACT

Disclosed herein are implants with threaded inserts and methods for attaching the same to the implants. The threaded insert may define a first external dimension and include an internally threaded hole to receive a fastener. The implant may include a receiving hole with a proximal portion having a proximal diameter and a distal portion having a distal diameter. The distal diameter may be greater than the proximal diameter and substantial the same as the first dimension of the insert to secure the insert in the receiving hole. A method of attaching a threaded insert to a receiving hole of an implant with an insertion tool is also disclosed.

20 Claims, 10 Drawing Sheets

(56) References Cited

U.S. PATENT DOCUMENTS

| | | |
|---|---|---|
| 1,940,075 A | 12/1933 | Caldwell |
| 2,077,712 A | 4/1937 | Roberts et al. |
| 2,761,735 A | 9/1956 | Berghoff |
| 2,826,483 A | 3/1958 | Kuhlmann |
| 2,910,598 A | 10/1959 | Schrotzberger |
| 2,959,835 A | 11/1960 | gates |
| 2,989,526 A | 6/1961 | Kerwin et al. |
| 3,090,210 A | 5/1963 | Groff |
| 3,171,721 A | 3/1965 | Stratheam et al. |
| 3,195,293 A | 7/1965 | Daily et al. |
| 3,200,221 A | 8/1965 | Traher |
| 3,244,175 A | 4/1966 | Sturges |
| 3,288,191 A | 11/1966 | Thorborg |
| 3,328,988 A | 7/1967 | Schmidt |
| 3,331,421 A | 7/1967 | Lambert |
| 3,378,838 A | 4/1968 | Romano |
| 3,383,415 A | 5/1968 | Carabateas |
| 3,394,281 A | 7/1968 | Lafferty |
| 3,418,824 A | 12/1968 | Beutel et al. |
| 3,421,161 A | 1/1969 | Stafford et al. |
| 3,421,162 A | 1/1969 | Diemond et al. |
| 3,441,989 A | 5/1969 | Clarkson et al. |
| 3,464,111 A | 9/1969 | Gillard |
| 3,464,192 A | 9/1969 | De Vries et al. |
| 3,504,068 A | 3/1970 | Zizlsperger et al. |
| 3,504,112 A | 3/1970 | Gruenberg |
| 3,504,188 A | 3/1970 | Ficker |
| 3,504,275 A | 3/1970 | Eller et al. |
| 3,504,280 A | 3/1970 | Byrd |
| 5,782,929 A * | 7/1998 | Sederholm .......... A61F 2/30744 623/22.34 |
| 6,228,121 B1 * | 5/2001 | Khalili ................ A61F 2/30749 623/22.36 |
| 9,351,839 B2 * | 5/2016 | Meridew .................... A61F 2/34 |
| 2004/0038179 A1 * | 2/2004 | Kumar .................... A61C 8/008 433/173 |
| 2006/0142872 A1 * | 6/2006 | Klotz .................... A61F 2/4059 623/23.44 |
| 2009/0254125 A1 * | 10/2009 | Predick .............. A61B 17/7037 606/264 |

* cited by examiner

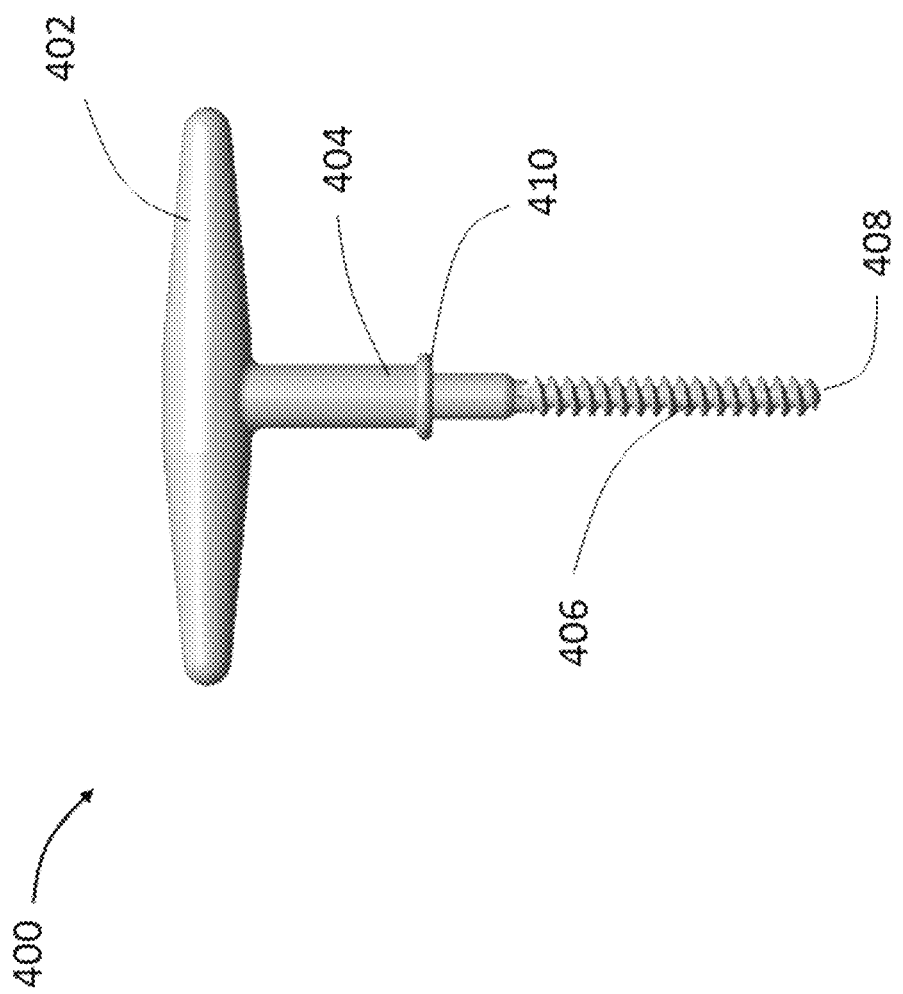

THREADED INSERT FOR IMPLANT

CROSS-REFERENCE TO RELATED APPLICATION

The present application claims the benefit of the filing date of U.S. Provisional Patent Application No. 62/574,407, filed on Oct. 19, 2017, the disclosure of which is hereby incorporated by reference.

FIELD OF INVENTION

The present invention relates to inserts for implants and methods for attaching the same, and in particular to a threaded insert and a method for attaching the same to an implant.

BACKGROUND OF THE INVENTION

Fasteners such as bone screws are typically used to secure implants to treat various bone maladies including fractures and deformities. In a typical example, one or more fasteners are inserted through bore holes in an implant and attached to the target bone portion. Stable fixation of the implant to ensure proper healing over time is critical. However, bone screw retention within the bone portion may be comprised in some instances resulting in implant detachment and improper implant placement. Consequently, bone screw loosening within the bone region may result in a loss of compressive force on the bone region by the implant leading to unsuccessful treatment. Bone screw loosening within the bone may be particularly exacerbated due to infections or other maladies which may weaken bone region at the bone screw insertion site.

Implants with threaded internal bores may provide better fixation whereby a threaded engagement between the bone screw and the implant further strengthens the implant-bone connection. The threaded engagement between the implant and the bone screw will prevent bone screw displacement or backout with reference to the implant. However, providing threaded internal bore holes on implants is generally difficult, especially for implants having long bore holes which may require specialized machining and tooling to cut internal threading. In many instances standardized implants may be provided with multiple bore holes intended to provide multiple fixation points depending on the needs of the surgical procedure. In these instances, a surgeon may only use one or some of the bore holes to insert fasteners to attach the implant to the bone region. Hence, providing threaded bore holes for unused fixation points will increase implant manufacturing cost and time.

Therefore, there exists a need for improved inserts to attach fasteners to implants and methods for attaching the same to the implant.

BRIEF SUMMARY OF THE INVENTION

Disclosed herein are threaded inserts for implants and methods for securing the same.

In a first aspect of the present invention, an implant having a body and an insert is provided. The body may include a hole extending therethrough along a first longitudinal axis. The hole may have a distal portion with a distal diameter and a proximal portion with a proximal diameter. The distal diameter may be greater than the proximal diameter. The insert may be configured to be housed within the hole of the body. The insert may have a proximal face and a distal face with an external wall extending therebetween. An aperture may extend from the proximal face to the distal face along a second longitudinal axis. The aperture may have internal threads to receive and threadingly engage with a fastener. At least a first dimension of the external wall measured normal to the hole may be greater than the proximal diameter and substantially the same as the distal diameter such that the insert when housed with the hole of the body may be located in the distal portion.

In accordance with the first aspect, the insert may be cylindrically shaped with an external diameter of the external wall defining the first dimension. The external wall may have external ridges to secure the insert to the distal portion of the body.

Further in accordance with the first aspect, the first longitudinal axis may be collinear to the second longitudinal axis when the insert is secured in the distal portion. The first longitudinal axis may be offset to the second longitudinal axis when the insert is secured in the distal portion.

A third longitudinal axis extending centrally from the proximal face to the distal face may be offset to the second longitudinal axis. The insert may be rotated from a first position to a second position within the distal portion such that in the first position, the first longitudinal axis may be collinear with the second longitudinal axis, and in the second positon, the first longitudinal axis may be offset to the second longitudinal axis.

Further in accordance with the first aspect, a lip may separate the distal portion from the proximal portion. The proximal face of the insert may contact the lip when the insert in secured in the distal portion. The proximal portion may include a first proximal portion and a second proximal portion. The second proximal portion may be disposed between the first proximal portion and the distal portion. The first proximal portion may have an expanding diameter across the second longitudinal axis, increasing in a direction away from the second proximal portion. A fourth longitudinal axis defined by a length of the fastener may be offset to the first and second longitudinal axes. The insert may be shaped according to any of a sphere, cuboid, cube, cone and pyramid. The implant may be an acetabular cup.

Still further in accordance with the first aspect, the insert may threadingly engage with an insertion tool such that when the insert is threadingly engaged with the insertion tool, rotation of the insertion tool may translate the insert within the implant. The external walls of the insert may have external threads to threadingly engage with internal threads of the proximal portion. The insert may be secured to the distal portion by any of interference fit, snap fit, adhesive bonding, and welding.

In a second aspect of the present invention, an implant having a body and an insert is provided. The body may have at least one throughbore extending along a first longitudinal axis. The throughbore may have a proximal recess with a first diameter and a distal recess with a second diameter greater than the first diameter. The insert may have a proximal face and a distal face with an external wall extending therebetween. The insert may have an aperture extending from the proximal face to the distal face along a second longitudinal axis. The aperture may have internal threads to receive and threadingly engage with a fastener. At least a first dimension of the external wall measured normal to the throughbore may be greater than the first diameter and substantially the same as the second diameter. The insert when housed with the throughbore of the body may be located entirely within the distal recess such that both the proximal and distal faces of the insert may be located within the distal recess.

In accordance with this second aspect, the external wall may have external ridges to secure the insert to the proximal recess of the body. The first longitudinal axis may be collinear to the second longitudinal axis when the insert is secured in the distal recess. The first longitudinal axis may be offset to the second longitudinal axis when the insert is secured in the distal recess.

A third aspect of the present invention is a method of attaching an insert to an implant body. A method in accordance with this aspect of the invention may include the steps of placing an insert at a distal end of receiving hole in an implant body, placing an insertion tool through a receiving hole and threadingly engaging a distal end of an insertion tool with the insert, and advancing the insert in a distal portion by rotating the insertion tool in a first direction until the proximal face of the insert contacts a lip. The insert may have a proximal face and a distal face with an external wall extending therebetween. A first hole may extend from the proximal face to the distal face along a first longitudinal axis. The first hole may have internal threads to receive and threadingly engage with a fastener. The implant body may have a receiving hole extending along a second longitudinal axis. The second hole may have a distal portion with a distal diameter and a proximal portion with a proximal diameter. The distal diameter may be greater than the proximal diameter. At least a first dimension of the external wall measured normal to the first hole may be greater than the proximal diameter and substantially the same as the distal diameter. The lip may separate the proximal portion from the distal portion. The insertion tool may have external threads to threadingly engage with the internal threads of the insertion tool.

BRIEF DESCRIPTION OF THE DRAWINGS

A more complete appreciation of the subject matter of the present invention and the various advantages thereof may be realized by reference to the following detailed description, in which reference is made to the following accompanying drawings:

FIG. 9 is a insertion tool according to another embodiment of the present invention.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
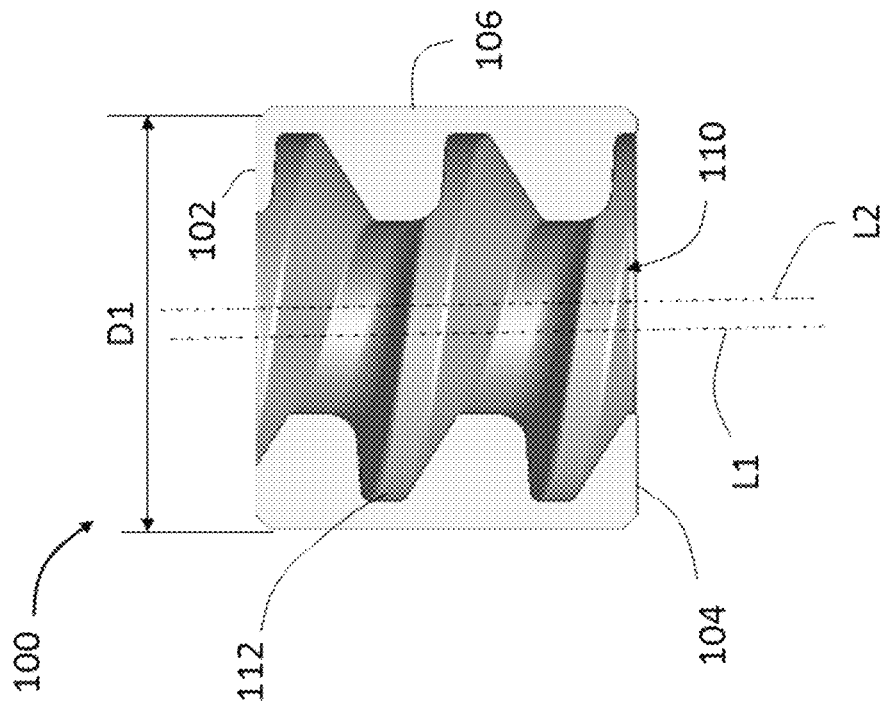
FIG. 1 is a front perspective view of an insert according to an embodiment of the present invention.

Referring now to FIG. 1, there is shown an insert 100 according to a first embodiment of the present invention. Insert 100 is cylindrical in shape with a distal face 104 and a proximal face 102. An exterior wall 106 extends between proximal face 102 and distal face 104 along a central longitudinal axis L2. Exterior wall includes ridges 108 extending in a proximal-distal direction which are configured to secure insert 100 to a receiving hole of an implant as more fully described below. A hole 110 having a longitudinal axis L1 extends from a center of proximal face 102 to a center of distal face 104.

Figure 2:
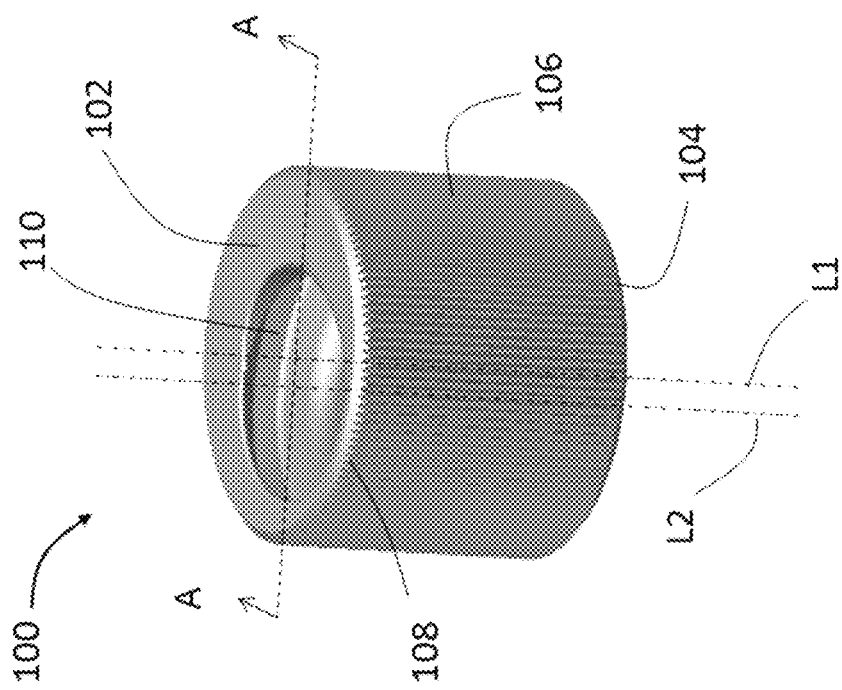
FIG. 2 is a side cross-sectional view along line A-A of the insert of FIG. 1.

FIG. 2 shows a cross-sectional view of insert 100. Hole 110 is acentrically positioned within insert 100 as best seen by the offset of longitudinal axis L1 of the insert and longitudinal axis L2 of hole 110. Internal threading 112 present in the interior of hole 112 as best shown in FIG. 2 is used to engage with a fastener or an insertion tool as more fully explained below. A length D1 defines the diameter of the insert 100. While a generally cylindrically shaped insert with a uniform diameter D1 is shown in this embodiment, other embodiments may be shaped according to a sphere, cuboid, cube, cone, pyramid or other suitable shapes.

Figure 3:
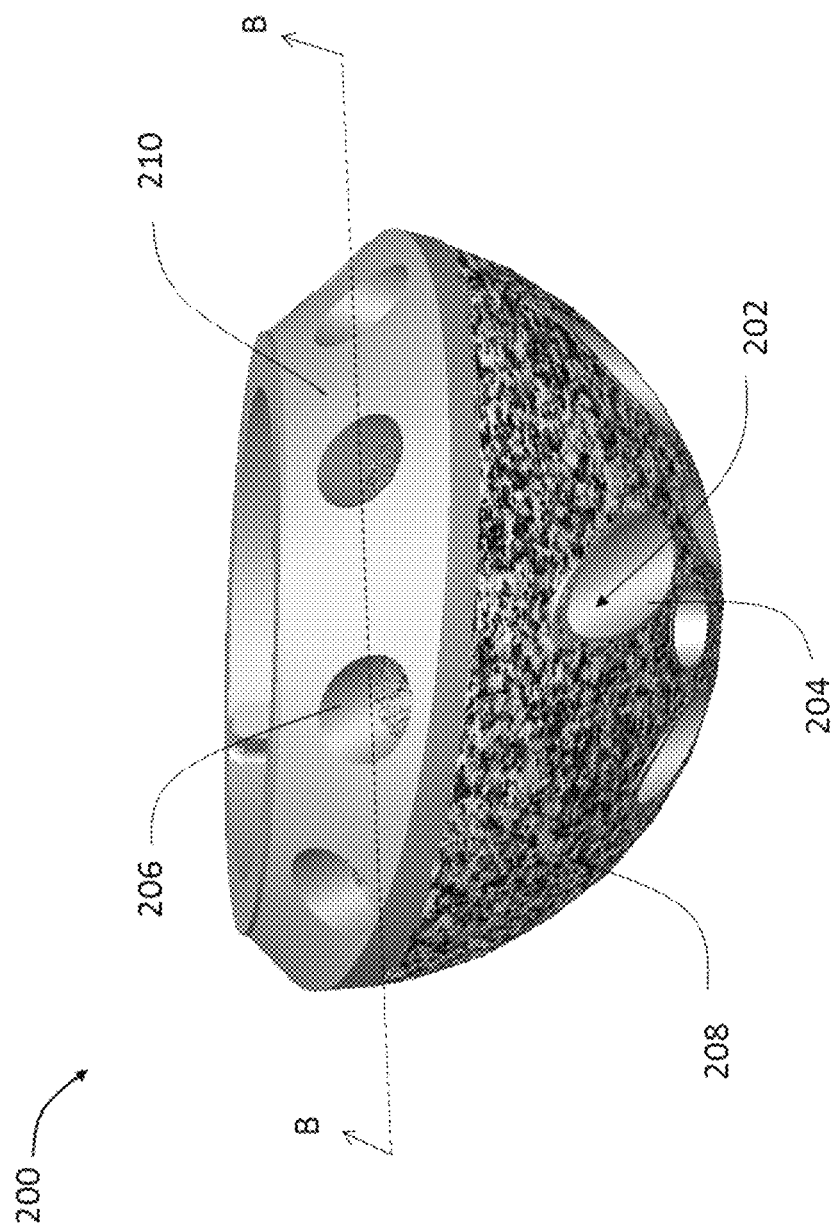
FIG. 3 is a front perspective view of an implant with the insert of FIG. 1.
Figure 4:
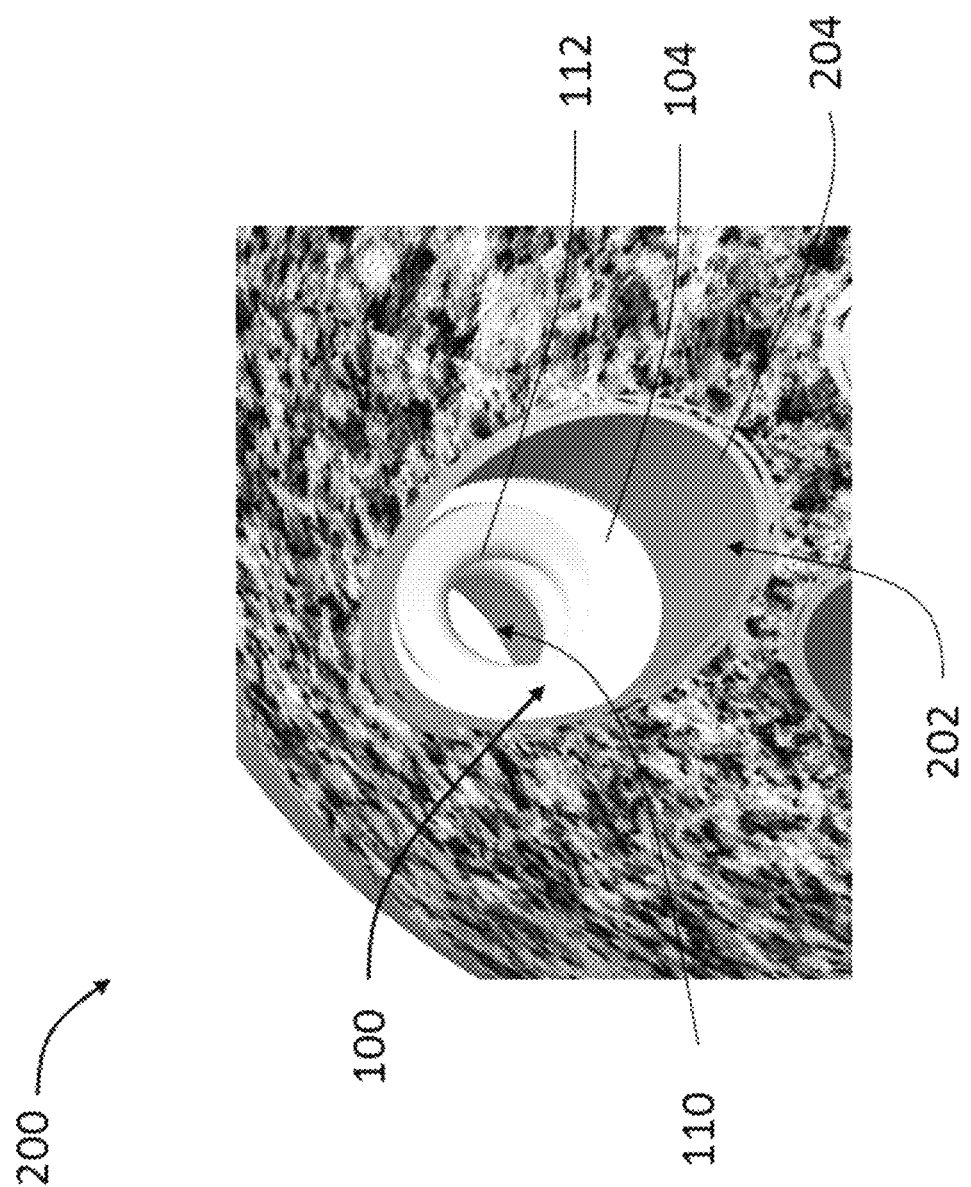
FIG. 4 is a partial bottom view of the implant of FIG. 3.

Referring now to FIGS. 3 and 4, there is shown a body of an implant 200 with insert 100. Implant 200 is an acetabular cup prosthesis or body having an annular base 210 with multiple receiving holes 202 to receive fasteners (not shown). Each receiving hole 202 has a proximal opening 206 at base 210 and a distal opening 204 at an outer convex surface 208. As best seen in FIG. 4, insert 100 can be secured within receiving hole 202.

Figure 5:
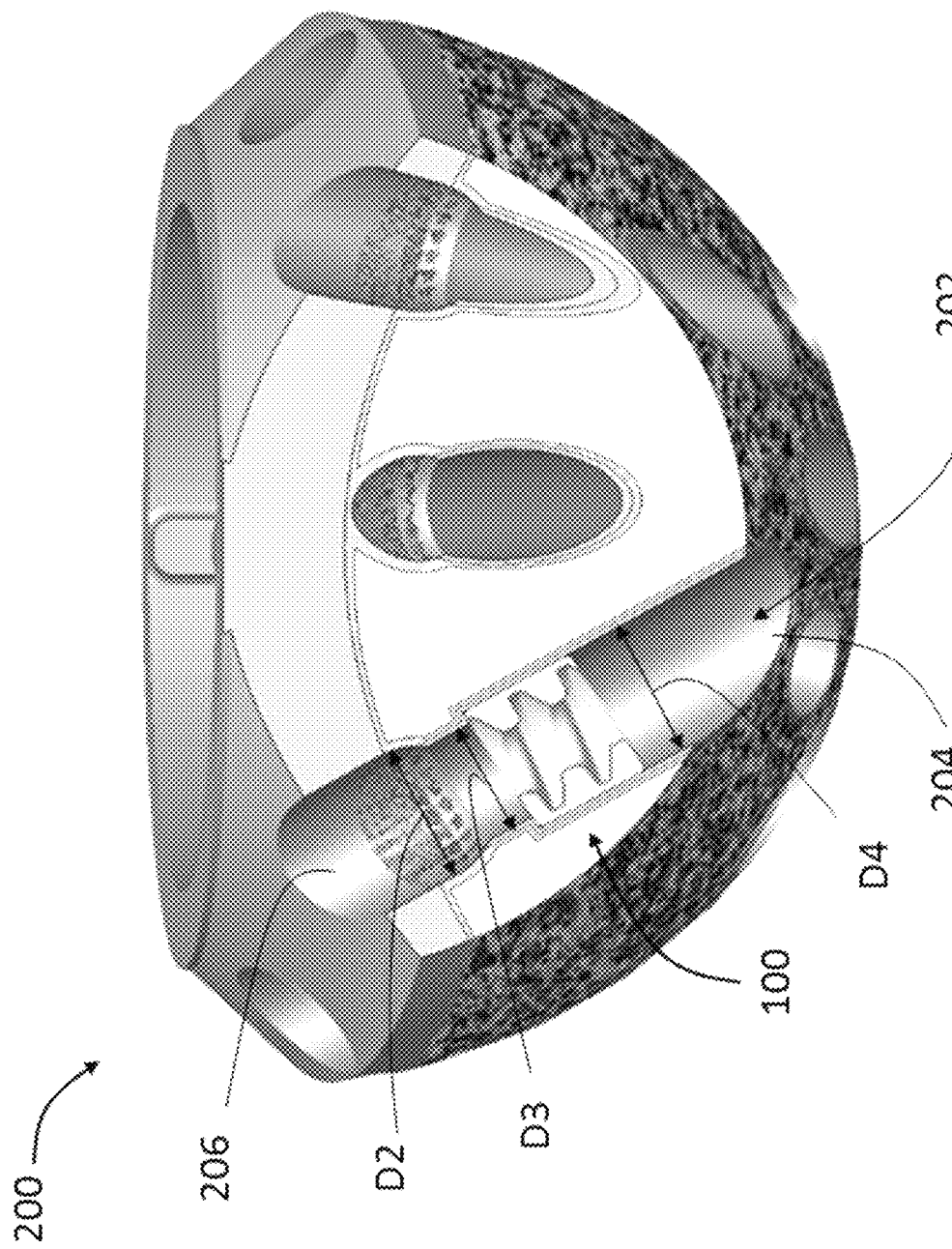
FIG. 5 is front cross-sectional view along line B-B of the implant of FIG. 3.
Figure 6:
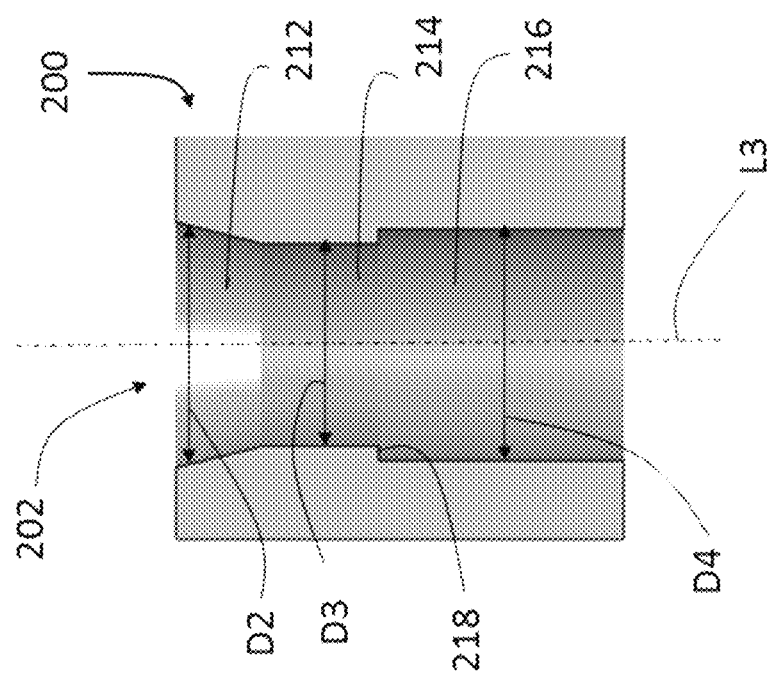
FIG. 6 is a side cross-sectional view of a receiving hole of the implant of FIG. 3.

FIG. 5 shows a side cross-sectional view of implant 200 and insert 100. Receiving hole 202 extends a long a central longitudinal axis L3 and has varying dimensions and regions to ensure that insert 100 is securely attached to implant 200. As best shown in FIG. 6, there are at least three distinct regions in receiving hole 202 to facilitate proper attachment of insert 100 to subsequently receive a fastener. A distal portion 216 defines a diameter D4, a central portion 214 defines a diameter D3 and a proximal portion 212 has a conical profile with varying dimensions. A proximal end of proximal portion 212 is attached to central portion 214 and has the same the diameter as diameter D3. Proximal portion 212 flares out in the distal direction defining a maximum diameter D2 at a distal end. Diameter D4 of distal portion 216 is greater than diameter D3 of central portion. A lip 218 separates distal portion 216 and central portion 214.

Figure 7:
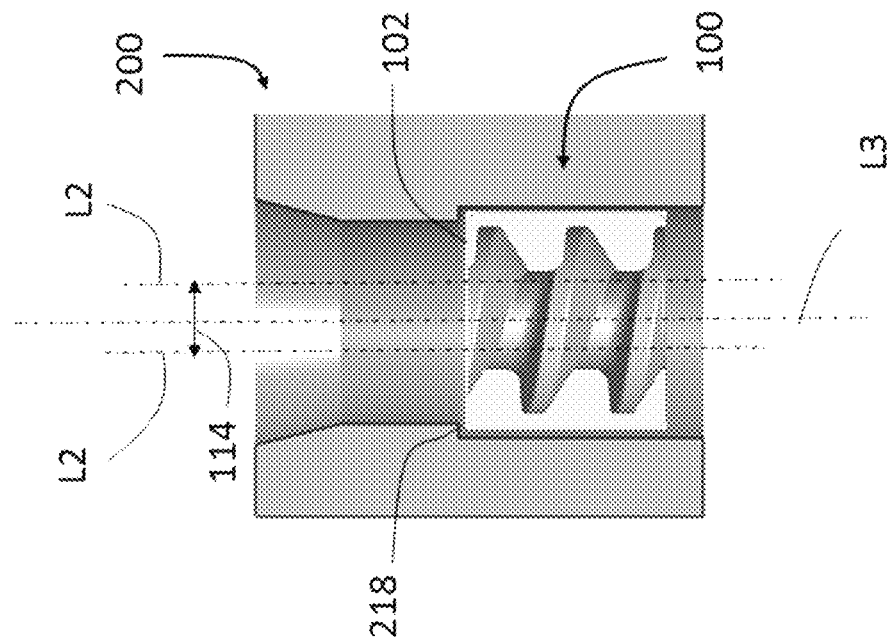
FIG. 7 is a side cross-sectional view of the receiving hole of FIG. 6 with the insert of FIG. 1.

Referring now to FIG. 7, there is shown a cross-sectional view of insert 100 secured in receiving hole 202. Diameter D1 of insert 100 is substantially the same or slightly greater than diameter D4 of distal portion 216. Therefore, insert 100 may be press fitted into distal portion 216 and secured by the resulting interference fit between insert 100 and distal portion 216. Ridges 108 on exterior wall 106 of insert 100 enhance the attachment between the insert and distal portion 216. Insert 100 can be distally advanced in distal portion 216 until proximal face 102 contacts lip 218 preventing further distal advancement. Longitudinal axis L2 of hole 110 can be positioned or moved with respect to longitudinal axis L3 of insert 100 as indicated by line 114 by rotating insert 100. Longitudinal axis L2 being offset to the center of the insert, can be positioned by rotating insert 100 to align hole axis L2 as desired. Alternatively, lip 218 and/or distal portion 216 may be configured to allow multiple positioning of axis L2 by rotating or moving insert 100 within the proximal portion. As shown in FIG. 7, insert 100 is positioned within receiving hole 202 to align longitudinal axis L2 with longitudinal axis L3.

Figure 8:
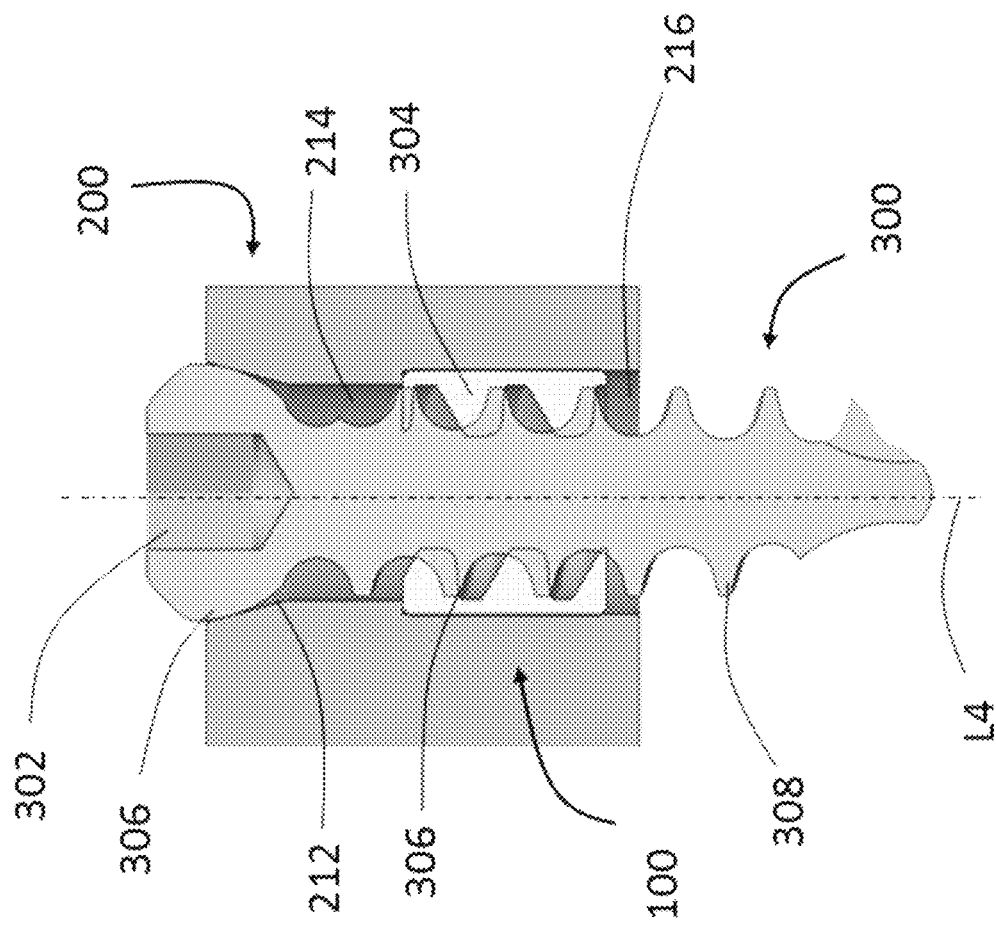
FIG. 8 is a side cross-sectional view of a fastener attached to the receiving hole of FIG. 7.

FIG. 8 shows a cross-sectional view of a fastener 300 secured to implant 200 by insert 100. Fastener 300 includes a head 306 with a drive 302 and a body with external threading 304 extending along a central longitudinal axis L4. External threading 304 is configured to threadingly engage with internal threading 112 of hole 110. As shown here, longitudinal axis L2, L3 and L4 are collinear allowing fastener 300 to be inserted normal to the receiving hole. Other embodiments may have inserts configured to allow for polyaxial attachment of fasteners with the insert and the implant. Fastener head 306 is shaped to conform to the conical profile of proximal portion 212. Contact between head 306 and proximal portion 212 can facilitate cold welding between the fastener and the implant over a period of time to secure engagement between them.

After fastener 300 is seated in position with implant through insert 100, a distal threaded portion 308 extends away from distal opening 204 as shown in FIG. 8. Distal threaded portion 308 can be attached to bone or soft tissue or to a second implant (not shown). A distal threaded portion 306 of fastener 300 being threadingly engaged with insert 100 and implant 200 prevents disengagement of the fastener from implant 200. Specifically, fastener backout in a distal direction from insert 100 is prevented by the threading engagement between distal threaded portion 306 with internal threading 112. Further, as more fully explained above, insert 100 cannot distally advance beyond lip 218. Hence, fastener 300 can be firmly secured to bone, tissue or a second implant at the distal end and simultaneously secured to an implant at a proximal end.

Inserts described herein may be made from polymers such as PEEK, carbon fiber reinforced PEEK, PAEK, UHMWPE, metals, ceramics, combinations of the foregoing, or other suitable materials that are biocompatible and possess sufficient strength and rigidity. Additive manufacturing techniques such as 3D printing may be used to fabricate inserts of the present invention. While a press fitting insert to form an interference fit with an implant is described here, other suitable attachment mechanisms may be used to secure insert within implant. For example, the exterior walls of the insert may have external threads to threadingly engage with corresponding threads on the receiving hole. Other attachment means may include welding techniques such as ultrasonic welding, the use of adhesives, snap fitting mechanisms or similar mechanisms. The internal threading of the insert may have varying thread patterns and dimensions to match suitable fastener threading profiles.

Referring now to FIG. 9, there is show an insertion tool 400 according to another embodiment of the present invention. Insertion tool 400 can be used to attach insert 100 to implant 200. Insertion tool includes a handle 402, a shank 404 and an externally threaded body 406. Handle 402 includes a grippable portion to allow an operator to grip and manipulate the tool as necessary. Shank 404 has a stopper 410 to limit distal-proximal advancement of threaded body 406. External threading 406 is configured to threadingly engage with internal threading 112 of insert 100 as more fully described below. Various dimensions of the insertion tool, stopper location and external threading characteristics can be varied to be used with specific implants and inserts.

Figure 10A:
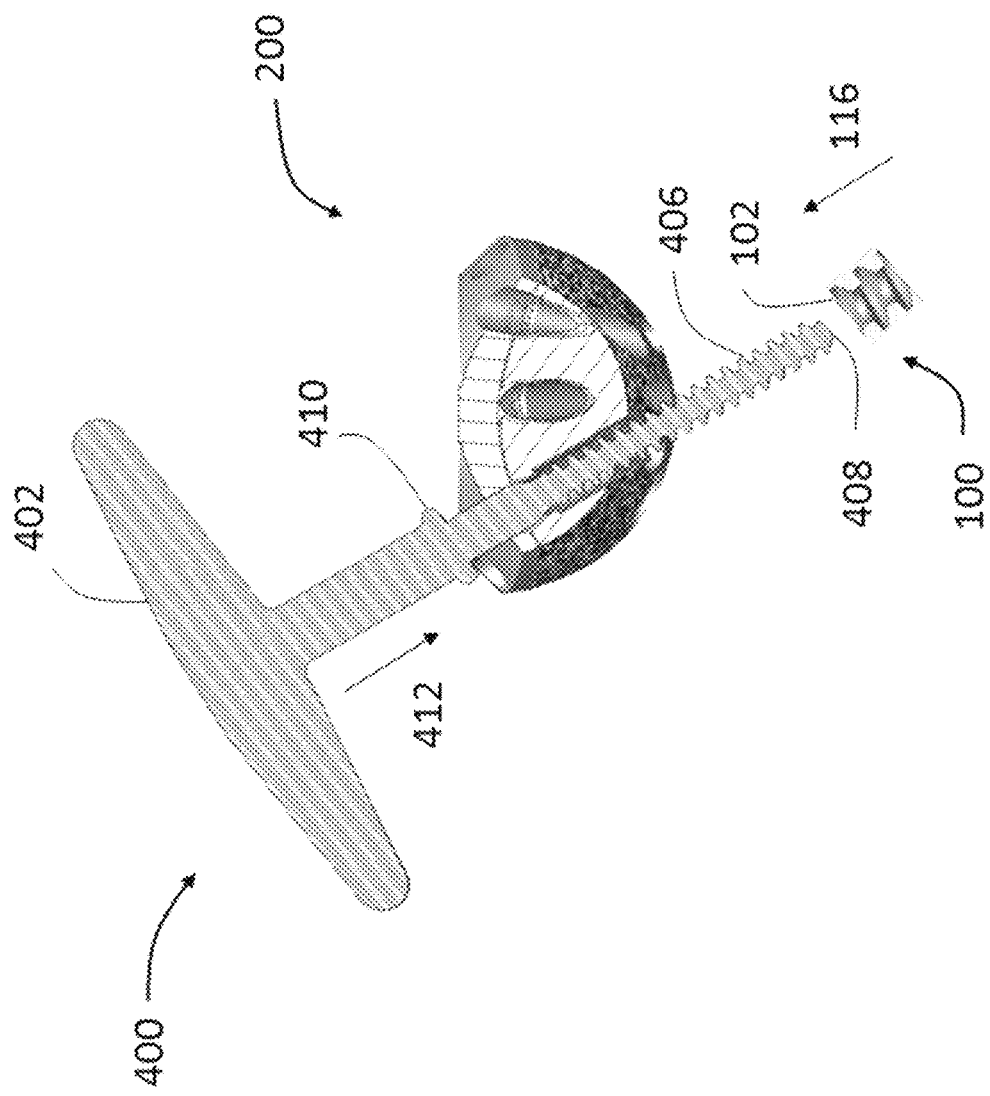
FIGS. 10A-C are side cross-sectional schematic illustrations of attaching the insert of FIG. 1 to the implant of FIG. 3 with the insertion tool of FIG. 9 according to another embodiment of the present invention.
Figure 10B:
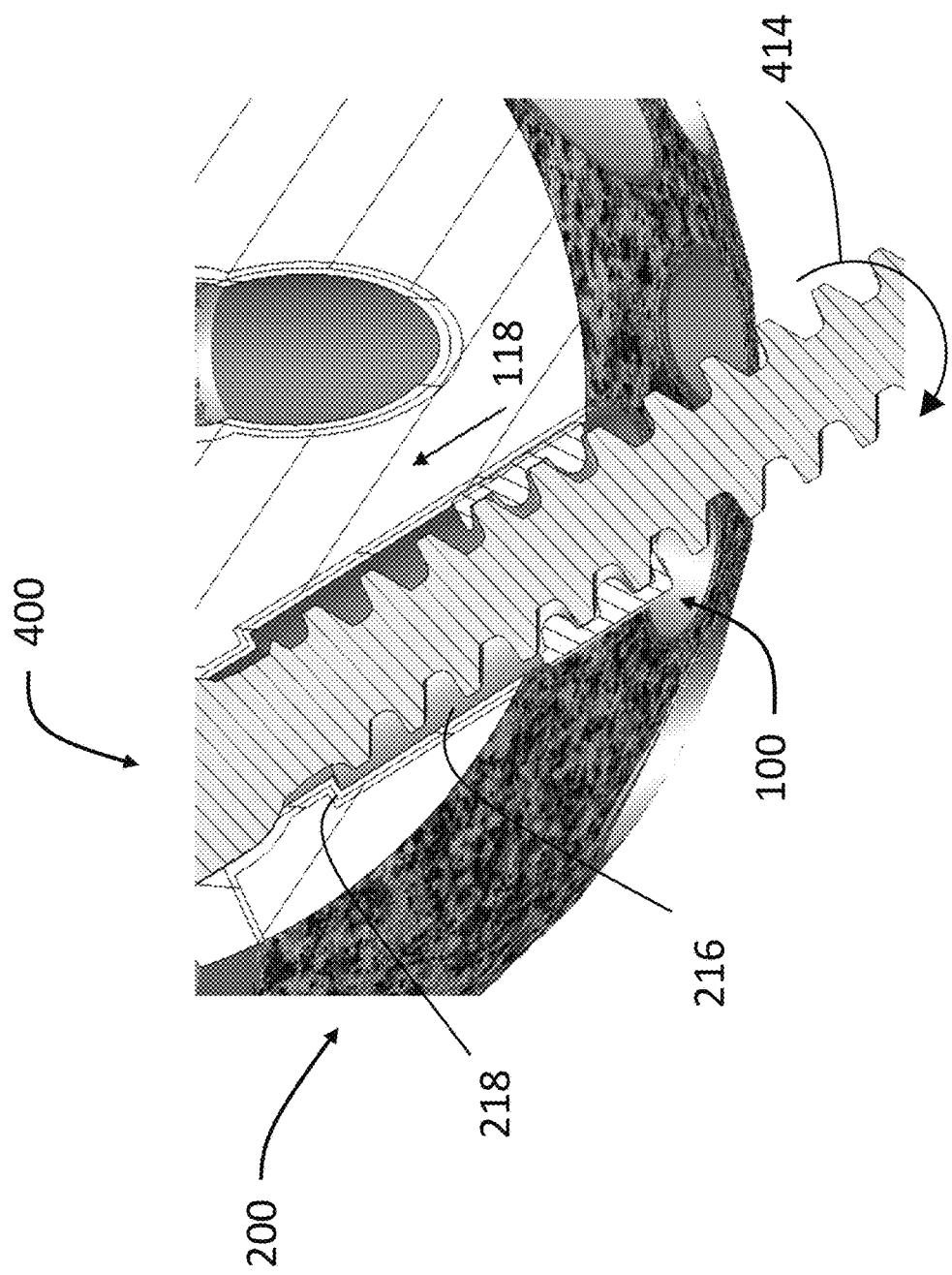
Figure 10C:
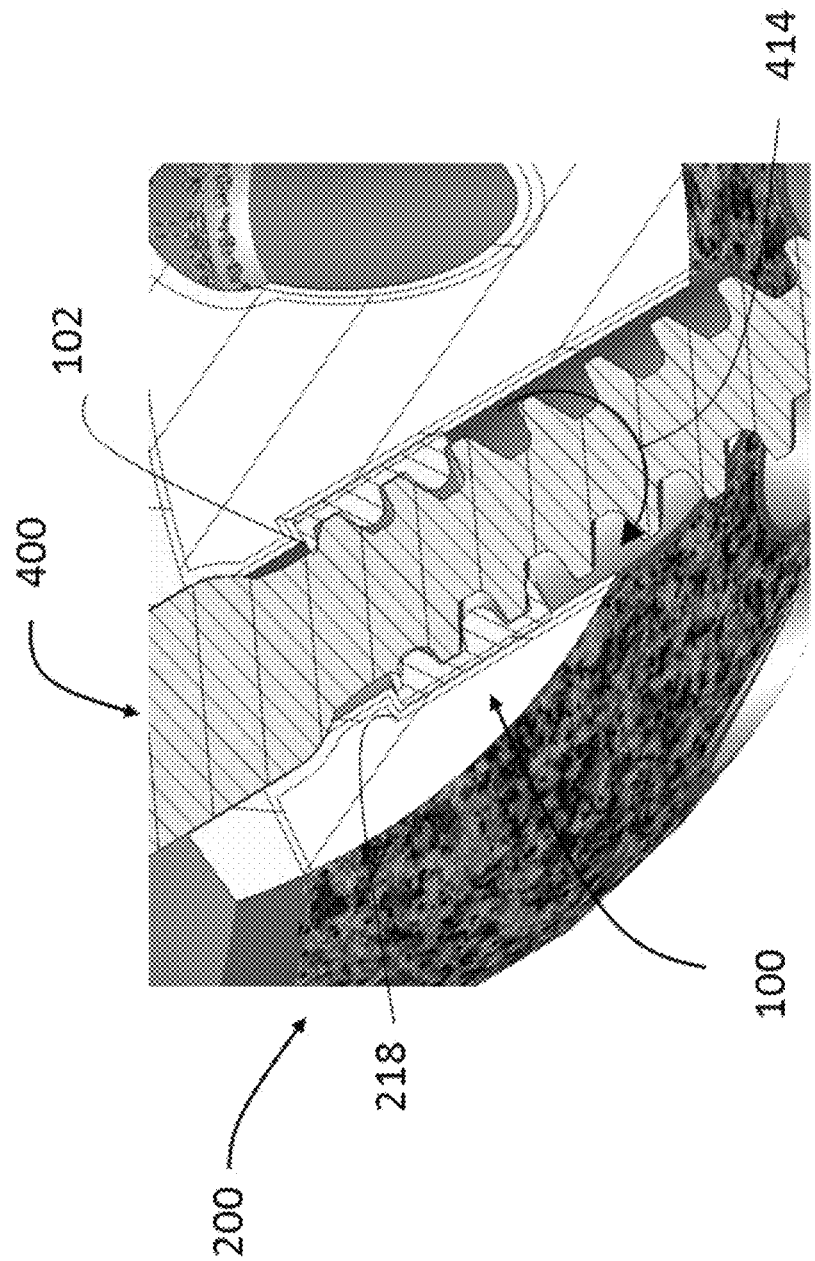

Referring now to FIGS. 10A-10C, there is shown method for attaching insert 100 to implant 200 with insertion tool 400 according to an embodiment of the present invention. Insertion tool 400 is selected such that external threading 406 can threadingly engage with internal threadingly 112 and the length of the insertion tool body is greater than the length of the receiving hole in the implant. Insertion tool 400 is inserted into receiving hole 202 from distal opening 204 as indicated by direction arrow 412 to allow a distal tip 408 to extend from implant 200. An operator may select any of the multiple receiving holes 202 on implant 200 depending on the desired fastener position location and angle. Proximal face 102 of insert 100 is placed in contact with distal tip 408 as shown by direction arrow 116 and threadingly engaged with the insertion tool as shown in FIG. 10A. Alternatively, proximal face 102 of insert 100 can be pushed into proximal opening to insert a portion of insert 100 in the receiving hole and then insertion tool 400 can be introduced from the distal opening to threadingly engage with insert 100.

Once distal tip 408 is threadingly engaged with insert 100 such that distal tip 408 extends past insert 100, insertion tool is rotated in a clockwise direction 414 as shown in FIG. 10B. Clockwise rotation of insertion tool 400 forces insert 100 distally into receiving hole 202 as indicated by direction arrow 118. As more fully explained above, diameter D1 of insert 100 being slightly larger than diameter D4 of distal portion 216 ensures an interference fit between the insert and the receiving hole. Clockwise rotation 414 of the insertion tool is continued until proximal face 102 of insert 100 contacts lip 218 as best shown in FIG. 10C. Further clockwise rotation of insertion tool 400 will retract the insertion tool from insert 100 which is now prevented from distal advancement by lip 218. Therefore, insertion tool 400 can be removed from receiving hole 202 by continuing to rotate it in a counterclockwise direction while leaving being insert 100 firmly secured to the proximal portion of implant 200.

While an acetabular cup implant is disclosed here, any other implant may be used with the inserts described in the present disclosure. Implants and inserts described herein may be made from polymers such as PEEK, carbon fiber reinforced PEEK, PAEK, UHMWPE, metals, ceramics, combinations of the foregoing, or other suitable materials that are biocompatible and possess sufficient strength and rigidity. Additive manufacturing techniques such as 3D printing may be used to fabricate implants and inserts of the present invention.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. An implant comprising:
   a body having a hole extending therethrough along a first longitudinal axis, the hole having a distal portion with a distal diameter and a proximal portion with a proximal diameter, the distal diameter being greater than the proximal diameter; and
   an insert configured to be housed within the hole of the body, the insert having a proximal face and a distal face with an external wall extending therebetween, an aperture extending from the proximal face to the distal face along a second longitudinal axis, the aperture having internal threads configured to threadingly engage a fastener,
   wherein at least a first dimension of the external wall measured normal to the hole is greater than the proximal diameter and substantially the same as the distal diameter such that the insert when housed with the hole of the body is located in the distal portion.

2. The implant of claim 1, wherein the insert is cylindrically shaped with an external diameter of the external wall defining the first dimension.

3. The implant of claim 2, wherein the external wall has external ridges to secure the insert to the distal portion of the body.

4. The implant of claim 1, wherein the first longitudinal axis is collinear to the second longitudinal axis when the insert is secured in the distal portion.

5. The implant of claim 1, wherein the first longitudinal axis is offset to the second longitudinal axis when the insert is secured in the distal portion.

6. The implant of claim 1, wherein a third longitudinal axis extending centrally from the proximal face to the distal face is offset to the second longitudinal axis.

7. The implant of claim 6, wherein the insert can be rotated from a first position to a second position within the distal portion such that in the first position, the first longitudinal axis is collinear with the second longitudinal axis, and in the second position, the first longitudinal axis is offset to the second longitudinal axis.

8. The implant of claim 1, wherein a lip separates the distal portion from the proximal portion.

9. The implant of claim 1, wherein the proximal face of the insert contacts the lip when the insert in secured in the distal portion.

10. The implant of claim 1, wherein the proximal portion includes a first proximal portion and a second proximal portion, the second proximal portion being disposed between the first proximal portion and the distal portion, the first proximal portion having an expanding diameter across the second longitudinal axis, increasing in a direction away from the second proximal portion.

11. The implant of claim 10, wherein a fourth longitudinal axis defined by a length of the fastener may be offset to the first and second longitudinal axes.

12. The implant of claim 1, wherein the insert is shaped according to any of a sphere, cuboid, cube, cone and pyramid.

13. The implant of claim 1, wherein the implant is an acetabular cup.

14. The implant of claim 1, wherein the insert is configured to threadingly engage with an insertion tool such that when the insert is threadingly engaged with the insertion tool, rotation of the insertion tool translates the insert within the implant.

15. The implant of claim 1, wherein the external walls of the insert have external threads to threadingly engage with internal threads of the proximal portion.

16. The implant of claim 1, wherein the insert is secured to the distal portion by any of interference fit, snap fit, adhesive bonding, and welding.

17. The implant of claim 1, wherein the first longitudinal axis is collinear to the second longitudinal axis when the insert is secured in the distal recess.

18. An implant comprising:
   a body having at least one throughbore extending along a first longitudinal axis, the throughbore having a proximal recess with a first diameter and a distal recess with a second diameter greater than the first diameter;
   an insert having a proximal face and a distal face with an external wall extending therebetween, the insert having an aperture extending from the proximal face to the distal face along a second longitudinal axis, the aperture having internal threads configured to threadingly engage a fastener,
   wherein at least a first dimension of the external wall measured normal to the throughbore is greater than the first diameter and substantially the same as the second diameter, and
   wherein the insert when housed with the throughbore of the body is located entirely within the distal recess such that both the proximal and distal faces of the insert are located within the distal recess.

19. The implant of claim 18, wherein the external wall has external ridges to secure the insert to the proximal recess of the body.

20. A method of attaching an insert to an implant body, the insert having a proximal face and a distal face with an external wall extending therebetween, a first hole extending from the proximal face to the distal face along a first longitudinal axis, the first hole having internal threads to receive and threadingly engage with a fastener, the implant body having a receiving hole extending along a second longitudinal axis, the second hole having a distal portion with a distal diameter and a proximal portion with a proximal diameter, the distal diameter being greater than the proximal diameter, wherein at least a first dimension of the external wall measured normal to the first hole is greater than the proximal diameter and substantially the same as the distal diameter, wherein a lip separates the proximal portion from the distal portion, the method comprising the steps of:
   placing the insert at a distal end of a receiving hole in the implant body;
   placing an insertion tool through the receiving hole and threadingly engaging a distal end of an insertion tool with the insert, the insertion tool having external threads to threadingly engage with the internal threads of the insertion tool; and
   advancing the insert in the distal portion by rotating the insertion tool in a first direction until the proximal face of the insert contacts the lip.

* * * * *